United States Patent [19]

Goertz et al.

[11] Patent Number: 4,859,756

[45] Date of Patent: Aug. 22, 1989

[54] POLYMERS OF OXYALKYLATED UNSATURATED QUATERNARY AMMONIUM SALTS, THEIR PREPARATION AND THEIR USE

[75] Inventors: Hans-Helmut Goertz, Freinsheim; Alfred Oftring, Ludwigshafen; Friedrich Vogel, Wachenheim, all of Fed. Rep. of Germany

[73] Assignee: BASF Aktiengesellschaft, Ludwigshafen, Fed. Rep. of Germany

[21] Appl. No.: 226,198

[22] Filed: Jul. 29, 1988

[30] Foreign Application Priority Data

Jul. 31, 1987 [DE] Fed. Rep. of Germany ....... 3725449
Jul. 31, 1987 [DE] Fed. Rep. of Germany ....... 3725428

[51] Int. Cl.$^4$ .............................................. C08F 26/06
[52] U.S. Cl. ................................... 526/263; 526/277; 526/304
[58] Field of Search ................ 526/277, 263, 312, 304

[56] References Cited

U.S. PATENT DOCUMENTS 3,385,839 5/1968 Honig et al. ........................ 526/304
4,666,886 5/1987 Baschang et al. ..................... 514/17
4,675,180 6/1987 Guenter ............................... 424/70

OTHER PUBLICATIONS

Chemistry of Heterocyclic Compounds, (1973), vol. 9, pp. 713–716, "Reaction of n-vinylazoles and n-vinylindole with halohydrins", G. Skvortsova, et al.

Primary Examiner—Joseph L. Schofer
Assistant Examiner—Jeffrey T. Smith
Attorney, Agent, or Firm—Oblon, Spivak, McClelland, Maier & Neustadt

[57] ABSTRACT

Polymers are obtained by polymerization of water-soluble monomers which contain one or more polymerizable olefinic double bonds and a quaternary nitrogen atom which is substituted by one or more hydroxyalkyl groups and are present in the form of halide-free salts, with or without further comonomers.

5 Claims, No Drawings

POLYMERS OF OXYALKYLATED UNSATURATED QUATERNARY AMMONIUM SALTS, THEIR PREPARATION AND THEIR USE

The present invention relates to polymers which are obtained by polymerization of water-soluble monomers which contain one or more polymerizable olefinic double bonds and a quaternary nitrogen atom substituted by one or more hydroxyalkyl groups and which are present as halide-free salts, with or without further comonomers, their preparation and their use.

EP-A2-00 98 802 describes the reaction of trialkylamines with ethylene oxide in the presence of acids in an aqueous medium to give quaternary ammonium salts. Quaternization of tertiary amines, which contain a polymerizable olefinic double bond, with ethylene oxide or another alkylene oxide is not disclosed.

G. G. Skvortsova et al. (Khim Geterots. Soed. (1973), 777–780; English translation, pages 713–716) describe the reaction of N-vinylazoles, e.g. N-vinylimidazole, with halohydrins to give corresponding vinylimidazolium salts. However, this method only permits the preparation of salts which contain halide as a counter-ion, or expensive anion exchange has to be carried out. In the process described in the stated publication, the N-vinylimidazole is reacted in a closed vessel directly with excess ethylene chlorohydrin by heating for 22 hours at 90° C. Even at temperatures of about 70° C. and with reaction times of 50 hours, there is virtually no conversion to the quaternary salt. Even with substituted chlorohydrins, it is impossible to obtain reasonable yields, and no reaction is obtained with fluorohydrin even on heating for 100 hours at 90° C.

The limitation that only salts which contain a halide as an anion have been described for industrial polymerization processes presents problems in many cases. Halide can cause serious corrosion problems, for example in processes for the preparation of cationic polymers in the presence of halide. It is therefore desirable to be able to rely on halide-free monomers for the preparation of halide-free cationic polymers for large-scale industrial processes. It is advantageous if the counter-ion, instead of being corrosive, actually has a protective effect, as is known to be the case, for example, for phosphite, phosphate, etc.

It is an object of the present invention to provide water-soluble cationic polymers which contain any anions except for the corrosive halides and are prepared from halide-free quaternary monomers having one or more polymerizable olefinic double bonds and a quaternary nitrogen atom which is substituted by one or more hydroxyalkyl groups, with or without further comonomers, the said polymers being intended for use, in particular, as conductivity resins, as flocculants or in cosmetic formulations.

We have found that this object is achieved, when water-soluble monomers having a polymerizable olefinic double bond and a quaternary nitrogen atom, of the formula I

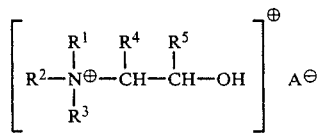

where $R^1$ is alkenyl of 2 to 4 carbon atoms, preferably allyl or methallyl, or a radical of the formula II

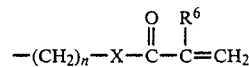

where n is an integer from 1 to 18, preferably from 2 to 6, X is oxygen or an NH group and $R^6$ is hydrogen or methyl, $R^2$ is alkyl of 1 to 18, preferably 1 to 4, carbon atoms or hydroxyalkyl of 2 to 18, preferably 2 to 4, carbon atoms, $R^3$ is alkenyl of 2 to 4 carbon atoms, preferably allyl or methallyl, or alkyl of 1 to 18, preferably 1 to 4, carbon atoms or hydroxyalkyl of 2 to 18, preferably 2 to 4, carbon atoms, or the radicals $R^1$, $R^2$ and $R^3$ together with the quaternary nitrogen atom form a 5-membered or 6-membered heterocyclic ring which is substituted by a polymerizable olefinic double bond, preferably a vinyl group, may contain a further nitrogen atom and may contain one or two alkyl radicals of 1 to 4 carbon atoms as further substituents, and $R^4$ and $R^5$ are each hydrogen or alkyl of 1 to 28, preferably 1 to 16, carbon atoms or are each methyl which is substituted by alkoxy where alkyl is of 1 to 10 carbon atoms, and $A^\ominus$ is one equivalent of an anion, except for halide, are used as starting monomers.

The preparation of the halide-free monomers does not form a subject of the invention. However, it is described in detail below since a large-scale industrial process for the preparation of the said monomers has not been described.

Specifically, in formula I, alkenyl radicals $R^1$ and $R^3$ of 2 to 4 carbon atoms are each in particular vinyl, allyl or methallyl.

$R^1$ in formula II is a radical derived from an acrylate, a methacrylate, an acrylamide or a methacrylamide. n is particularly preferably 2 or 3.

Alkyl radicals $R^2$ and $R^3$ of 1 to 18 carbon atoms are each straight-chain or branched, for example methyl, ethyl, propyl, isopropyl, butyl, isobutyl, octyl, lauryl, cetyl and stearyl.

Particularly noteworthy alkyl radicals of 1 to 4 carbon atoms are methyl and ethyl.

Examples of straight-chain or branched hydroxyalkyl radicals $R^2$ and $R^3$ are hydroxyethyl, hydroxypropyl, hydroxybutyl, hydroxyoctyl, hydroxydodecyl, hydroxyhexadecyl and hydroxyoctadecyl.

Particularly noteworthy hydroxyalkyl radicals of 2 to 4 carbon atoms are hydroxyethyl and hydroxypropyl, as formed as reaction products of ethylene oxide and propylene oxide in the preparation.

Where $R^1$, $R^2$ and $R^3$ together with the quaternary nitrogen atom form a vinyl-substituted heterocyclic ring, the compound of the formula I contains, in particular, a 2- or 4-vinylpyridine ring or a N-vinylimidazole ring which may be substituted at the carbon atoms by one or two alkyl radicals of 1 to 4 carbon atoms, preferably methyl. The relevant compounds are preferably N-vinylimidazole and N-vinyl-2-methylimidazole.

$R^4$ and $R^5$ are, in particular, each hydrogen, and preferably only one of the radicals $R^4$ or $R^5$ is replaced by alkyl or alkoxymethyl.

Examples of alkyl radicals $R^4$ and $R^5$ are methyl, ethyl, hexyl, decyl, tetradecyl and hexadecyl. Noteworthy radicals are methyl, ethyl and tetradecyl.

Examples of alkoxymethyl radicals are methoxymethyl, ethoxymethyl, propoxymethyl, butoxymethyl, isopropoxymethyl, isobutoxymethyl, 2-ethylhexyloxymethyl, octyloxymethyl and decyloxymethyl, methoxymethyl, ethoxymethyl and 2-ethylhexyloxymethyl being noteworthy.

The anion is one equivalent of an anion with the exception of halide. Phosphate, sulfate, nitrate, phosphite, hypophosphite and phosphonate are particularly suitable. In the case of polybasic inorganic or organic acids, the anions of the individual dissociation stages are of course also suitable, e.g. phosphate, hydrogen phosphate and dihydrogen phosphate. Suitable anions of an organic acid in equivalent amounts are, in particular, anions of monobasic alkanecarboxylic acids of 1 to 18 carbon atoms where alkyl may be substituted by a hydroxyl group, anions of dibasic or tribasic saturated organic carboxylic acids which have a total of 2 to 10 carbon atoms and are unsubstituted or substituted by one or more hydroxyl groups, and anions of aromatic carboxylic acids, for example formate, acetate, oxalate, benzoate, lactate, glycolate, malate, citrate and tartrate.

On the basis of the noteworthy and preferred meanings, the preferred compounds of the formula I are derived from basic esters and from amides of acrylic or methacrylic acid which are substituted by basic radicals, from allylamine derivatives and from vinylimidazole compounds.

The compounds of the formula I are prepared by reacting an amine of the formula III

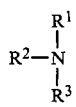   III where $R^1$, $R^2$ and $R^3$ have the meanings stated for formula I, with an epoxide of the formula IV

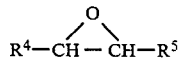   IV $R^4$ and $R^5$ have the meanings stated for formula I, in aqueous solution in the presence of an acid corresponding to the anion $A\ominus$ at a pH of from 7 to 10 and at from 10° to 90° C.

The amines of the formula III are known or can be prepared by a conventional method. They are tertiary amines, which are reacted with an epoxide of the formula IV.

In exceptional cases, a secondary or primary amine may be used as the starting material, in particular when one of the radicals $R^2$ or $R^3$ or both these radicals is or are a hydroxyalkyl radical which is identical to the hydroxyethyl radical carrying the substituents $R^4$ and $R^5$.

In the reaction of an amine of the formula III with an epoxide of the formula IV the preferred pH range is from 8.5 to 9.5 and the preferred temperatures are 40°–70° C., from 1 to 2, preferably from 1 to 1.5, moles of epoxide being used per mole of amine of the formula III.

Where secondary amine is used, from 2 to 3, preferably from 2 to 2.5, moles of epoxide are employed. In the case of primary amines, from 3 to 4, preferably from 3 to 3.5, moles of epoxide are used.

The reaction is advantageously carried out in an aqueous medium under atmospheric or superatmospheric pressure, the concentration of the reactants advantageously being from 10 to 80, in particular from 20 to 70, % by weight, based on the total weight of the reaction mixture.

The reaction can be carried out by initially taking the amine and the epoxide in water together and carrying out the reaction until the pH remains constant at a pH to be fixed with the particular acid, or, preferably, by adding the epoxide, in pure form or dissolved or emulsified in water, dropwise to an aqueous amine solution at a certain pH.

If necessary, the ammonium salt is obtained from the ammonium base when the reaction is complete by adding the acid corresponding to the anion $A\ominus$.

The resulting quaternary unsaturated ammonium compounds can preferably be further used directly in aqueous solution or can be isolated, for example by spray drying or freezing out.

On the basis of the abovementioned preferred meanings, the preferably reacted amines of the formula III are the compounds of the formula V

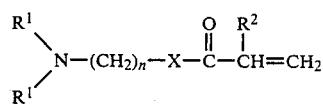   V where $R^1$ is alkyl of 1 to 4 carbon atoms, $R^2$ is hydrogen or methyl, X is oxygen or an NH group and n is 2 or 3, or allylamines of the formula VI

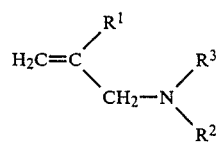   VI where $R^1$ is hydrogen or methyl, $R^2$ is alkyl of 1 to 4 carbon atoms or hydroxyalkyl of 2 to 4 carbon atoms and $R^3$ is allyl, methallyl or alkyl of 1 to 4 carbon atoms or hydroxyalkyl of 2 to 4 carbon atoms, or vinylimidazoles of the formula VII

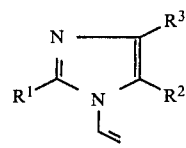   VII where $R^1$, $R^2$ and $R^3$ are each hydrogen and one of the radicals $R^1$ to $R^3$ may be methyl.

In the preferred epoxides of the formula IV, $R^4$ and $R^5$ are each hydrogen or one of the radicals $R^4$ or $R^5$ is methyl, ethyl, tetradecyl, methoxymethyl, ethoxymethyl or 2-ethylhexyloxymethyl.

Accordingly, examples of starting compounds for monomers of the formula I are dimethylaminoethyl acrylate, dimethylaminoethyl methacrylate, diethylaminoethyl acrylate, diethylaminoethyl methacrylate, dimethylaminopropylacrylamide, N-methyldiallylamine, allylamine, diallylamine, N-vinylimidazole and N-vinyl-2-methylimidazole.

Examples of epoxides are ethylene oxide, propylene oxide, 1-butylene oxide, 2-butylene oxide, 2-ethylhexyl propylene-2-oxirane ether, 1,2-epoxyhexadecane, methoxymethyloxirane and ethoxy methyloxirane.

Examples of preferred anions are phosphate, sulfate, formate, acetate, glycolate, oxalate, lactate and citrate, if necessary in the form of hydrogen anions.

Examples of the preparation of monomers of the formula I

EXAMPLE 1

45 g (1.02 moles) of ethylene oxide were added dropwise to a solution of 94 g (1 mole) of N-vinylimidazole in 150 g of water in the course of 3.5 hours at 40° C. The pH was kept at 9–9.5 by means of 85% strength phosphoric acid.

Stirring was then continued for a further 4 hours at 40° C. and at a pH of 9. After this time, no more vinylimidazole could be detected chromatographically and no more ethylene oxide could be found potentiometrically.

The pH was then brought to 5.5 with phosphoric acid. A total of 60 g of 85% strength phosphoric acid was consumed. 345 g of a roughly 55% strength clear aqueous solution of the ammonium salt of the formula

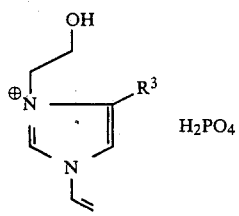

were obtained. Instead of phosphoric acid, other acids stated in the description, such as sulfuric acid, lactic acid and citric acid, can be used in a similar manner.

EXAMPLE 2

Example 1 was carried out in a similar manner using 81 g (1.4 moles) of propylene oxide, instead of ethylene oxide, in 700 g of water.

After the end of the reaction, the clear solution was freed from unconverted oxide by distillation under reduced pressure.

420 g of a roughly 57% strength solution of the ammonium salt of the formula

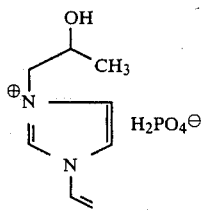

were obtained.

EXAMPLE 3

62 g (1.4 moles) of ethylene oxide were added dropwise at 45° in the course of 1.5 hours to a solution of 157.2 g (1 mole) of dimethylaminoethyl methacrylate in 700 g of water, the pH being kept at 9–9.5 with 85% strength phosphoric acid. Stirring was then continued for 2 hours at 45° C. and at a pH of 9. The resulting solution was brought to pH 5 with phosphoric acid. 986 g of a roughly 25% strength aqueous solution of the ammonium salt of the formula

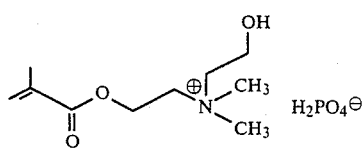

were obtained.

EXAMPLE 4 62 g (1.4 moles) of ethylene oxide were added dropwise at 35° in the course of 4 hours to an emulsion of 83.1 g (1 mole) of methyldiallylamine in 700 g of water. The pH was kept at 9.5 with 25% strength sulfuric acid. After stirring had been continued for a further 5 hours at 40° C. and at a pH of 9.0, the pH was brought to 5 with sulfuric acid.

After the aqueous clear solution had been concentrated, 330 g of a roughly 55% strength solution of the compound

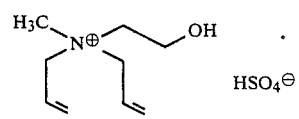

resulted.

EXAMPLE 5

47 g (0.5 mole) of N-vinylimidazole and 93 g (0.5 mole) of 2-ethylhexyl propylene-2-oxirane ether in 400 g of water were initially taken. A pH of 8.5 was maintained for 5 hours at 60° C. using 85% strength phosphoric acid. After the pH had been brought to 5, 565 g of a roughly 30% strength clear aqueous solution of

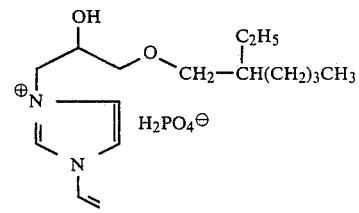

resulted.

The monomers of the formula I can advantageously be used for the preparation of water-soluble cationic polymers in the form of homopolymers or copolymers.

The present invention therefore relates to polymers which are obtained by polymerization of monomers of the formula I, as water-soluble homopolymers or as watersoluble copolymers of from 2 to 98% by weight of a monomer of the formula I and from 98 to 2% by weight of a polymerizable water-soluble unsaturated comonomer, the percentages being based on the total weight of the monomers, their preparation by free radical polymerization, in particular in aqueous solution, and their use.

In accordance with the statements about the monomers of the formula I, homopolymers and copolymers having the noteworthy and preferred meanings for the formula I are preferred.

Examples of homopolymers are poly-[2-(dimethylhydroxyethylammonio)-ethyl methacrylate dihydrogen phosphate] and poly-(N-vinyl-N'-hydroxypropylimidazolium dihydrogen phosphate) and poly-[2-

(hydroxyethyldimethylammonio)-ethyl methacrylate sulfate]and the corresponding phosphate, poly-[2-(hydroxypropyldimethylammonio)-ethyl methacrylate hydrogen phosphate], poly-[2-(hydroxyethyldiethylammonio)-ethyl acrylate lactate]and the corresponding phosphate, poly-[2-(hydroxypropyldiethylammonio)-ethyl acrylate acetate]and the corresponding phosphate, poly-[2-hydroxyethyldimethylammonio)-propyl methacrylate phosphate], poly-[N-(hydroxybutyldimethylammonio)-propyl methacrylamide citrate]and the corresponding phosphate, poly-[diallyldihydroxyethylammonium phosphite]and the corresponding phosphate, poly-[diallylmethylhydroxyethylammonium phosphate], poly-[allyltris(hydroxypropyl)ammonium succinate]and the [corresponding phosphate,]poly-[1-vinyl-3-hydroxybutyl]-imidazolium phosphate, poly-[1-vinyl-3-hydroxyethylimidazolium phosphate]and poly-[1-vinyl-2-methyl-3-hydroxypropylimidazolium benzoate]and the corresponding phosphate.

Poly-(diallylhydroxyethylmethylammonium hydrogen sulfate) and poly-(N-vinyl-N'-hydroxyethylimidazolium dihydrogen phosphate) are preferred.

The monomers used as water-soluble, unsaturated comonomers in the preparation of copolymers are, for example, the tertiary amines of the formula III from which the quaternary monomers of the formula I are derived, e.g. dimethylaminoethyl acrylate, dimethylaminoethyl methacrylate, diethylaminoethyl acrylate, diethylaminoethyl methacrylate, dimethylaminopropylacrylamide, N-methyldiallylamine, allylamine, diallylamine, N-vinylimidazole and N-vinyl-2-methylimidazole.

Other examples are acrylamide and methacrylamide, N-methylolacrylamide and N-methylolmethacrylamide, hydroxyalkyl acrylates and hydroxyalkyl methacrylates where hydroxyalkyl is of 2 to 4 carbon atoms, such as hydroxyethyl (meth)acrylate, hydroxypropyl (meth)acrylate, if desired in the form of their industrial mixtures, and polyethylene glycol (meth)acrylates containing from 2 to 50 ethylene oxide units.

Preferred comonomers are N-vinylamides, such as N-vinylpyrrolidone, N-vinylcaprolactam, N-vinylformamide, N-vinylacetamide and N-methyl-N-vinylacetamide, and hydroxyalkyl acrylates and methacrylates where hydroxyalkyl is of 2 to 4 carbon atoms.

Water-insoluble comonomers, such as styrene, α-olefins, such as pentene or butene, alkyl acrylates and methacrylates where alkyl is of 1 to 18 carbon atoms, or vinyl carboxylates where the carboxylate radical is of 2 to 10 carbon atoms, such as vinyl acetate or vinyl propionate, may also be copolymerized with the monomers of the formula I.

These comonomers may be present as copolymerized units in an amount of from 5 to 50% by weight, based on the total weight of the monomers.

It is particularly preferable to use monomers of the formula I for the preparation of homopolymers or of water-soluble copolymers of from 98 to 2% by weight of a monomer of the formula I with from 2 to 98% by weight of a monomer from the group consisting of N-vinylpyrrolidone, 2-hydroxyethyl acrylate and 2-hydroxypropyl acrylate (industrial mixture), the percentages being based on the total weight of the monomers.

The homopolymers and copolymers are prepared by conventional free radical polymerization, in particular in aqueous solution.

The polymerizations are advantageously carried out in 10–70% strength by weight aqueous solution in the presence of free radical initiators in an amount of from 0.1 to 3.0%, based on the weight of the monomers, and at from 40 to 100° C.

Suitable free radical initiators are hydrogen peroxide and inorganic persulfates, as well as organic compounds of the peroxide or azo type. Examples of suitable organic peroxides are dicyclohexyl peroxydicarbonate, dibenzoyl peroxide, dilauroyl peroxide, tert.-butyl perpivalate, tert.-butyl-2-ethylhexanoate, and suitable azo compounds are 2,2'-azobis-(2-amidinopropane) hydrochloride and 2,2'-azobis-(4-cyanopentanoic acid).

The free radical initiators used need not necessarily be water-soluble. Water-insoluble initiators can, for example, be dissolved in a lower alcohol or metered in directly without a solvent. The choice of the initiator is advantageously based, inter alia, on the polymerization temperature, which is preferably from 40 to 100° C.

The molecular weight of the polymer can, if desired, be controlled in a conventional manner, for example by adding regulators to the reaction mixture. Examples of suitable regulators are lower alcohols. However, it is also possible to use other suitable compounds, such as sulfur compounds, e.g. 2-mercaptoethanol, butyl mercaptan, dodecyl mercaptan, thioglycolic acid, thioacetic acid or thiolactic acid, halogen compounds, such as carbon tetrachloride or 1,1,1-tribromopropane, and formic acid and its derivatives.

The K value of the resulting polymer, which is a measure of the molecular weight, is obtained by suitable choice of regulator, initiator, polymerization temperature and monomer concentration. The K value of the homopolymers and copolymers obtained are advantageously from 10 to 150, measured in a 1% strength by weight aqueous solution at 25° C. by the Fikentscher method.

The resulting polymers have a wide range of uses, for example as conductivity resins, as flocculants, in the cosmetics industry, for example as hair conditioners, and as assistants in oil production, etc.

Their use in the cosmetics industry is particularly noteworthy. When used in hair sprays, it can be shown that there is substantial superiority over conventional cationic polymers with regard to corrosion. A practical formulation for a cosmetic hair foam is given in the Use Example. This formulation permits good wet and dry combability.

Examples of the preparation of novel polymers

EXAMPLE 6

A mixture of 115 g of N-vinylpyrrolidone, 148 g of monomer solution according to Example 1 and 130 ml of water was brought to pH 8.0 with about 70 ml of 10% strength by weight sodium hydroxide solution, and served as feed 1. Feed 2 consisted of 1.37 g of tert.-butyl perpivalate in 50 g of isopropanol. 150 ml of water, 30 ml of feed 1 and 3 ml of feed 2 were initially taken in a 1 glass apparatus and polymerized with stirring at 70° C. for 10 minutes. At this temperature, feed 1 was then added in the course of 4 hours and feed 2 in the course of 6 hours, and stirring was continued for one hour. Distilling off the isopropanol gave a slightly cloudy solution of a polymer which had a K value of 66 and became clear on further dilution with water.

EXAMPLE 7

120 g of a monomer solution according to Example 3 were diluted with 50 ml of water and brought to pH 8.5 with about 20 ml of 10% strength by weight sodium hydroxide solution. The resulting solution served as feed 1. 120 g of N-vinylpyrrolidone served as feed 2. Feed 3 was a solution of 0.75 g of tert.-butyl perpivalate in 50 g of isopropanol. 175 g of water, 15 ml of feed 1, 10 ml of feed 2 and 2.5 ml of feed 3 were initially taken in a 1 l glass apparatus equipped with a stirrer and feed vessels, and polymerization was carried out with stirring at 70° C. for 10 minutes. At this temperature, feeds 1 and 2 were then added in the course of 4 hours and feed 3 in the course of 6 hours, and stirring was continued for 1 hour. Distilling off the isopropanol gave a cloudy 35% strength solution of a having a K value of 61.

EXAMPLE 8

A mixture of 120 g of monomer solution according to Example 2, 30 g of hydroxypropyl acrylate and 60 g of water was brought to pH 7.0 with about 20 ml of 10% strength sodium hydroxide solution and served as feed 1. Feed 2 was a solution of 0.7 g of tert.-butyl perpivalate in 50 g of isopropanol. 60 ml of water, 20 ml of feed 1 and 3 ml of feed 2 were initially taken in a 0.5 l glass apparatus equipped with a stirrer and feed vessels, and polymerization was carried out at 70° C. for 10 minutes. At this temperature, feed 1 was then added in the course of 4 hours and feed 2 in the course of 6 hours and stirring was continued for 1 hour. Distilling off the isopropanol gave a virtually clear solution of a polymer of K value 28.

EXAMPLE 9

1.6 g of 2,2'-azobis-(2-amidinopropane) hydrochloride were dissolved in 100 g of a monomer solution according to Example 4, and the stirred solution was heated at 70° C. for 4 hours. A polymer solution having a K value of 14 was obtained.

EXAMPLE 10

125 g of a monomer solution according to Example 5 were mixed with 66 g of N-vinylpyrrolidone and 125 g of water and brought to pH 8.0 with about 10 ml of 10% strength sodium hydroxide solution. The solution served as feed 1. Feed 2 was a solution of 0.7 g of tert.-butyl perpivalate in 50 g of isopropanol. 65 g of water, 20 ml of feed 1 and 3 ml of feed 2 were initially taken in a 0.5 l glass apparatus and polymerized at 70° C. for 10 minutes with stirring. Thereafter, feed 1 was added in the course of 4 hours and feed 2 in the course of 6 hours at the same temperature, and stirring was continued for a further hour. Distilling off the isopropanol gave a cloudy polymer solution.

EXAMPLE 11

A mixture of 123 g of a 52% strength monomer solution prepared similarly to Example 1 but using sulfuric acid instead of phosphoric acid, 90 g of N-vinylpyrrolidone, 0.3 g of 2-mercaptoethanol and 140 ml of water was brought to pH 7.5 with about 7 ml of 10% strength sodium hydroxide solution and served as feed 1. Feed 2 was a solution of 1.1 g of 2,2'-azobis-(2-amidinopropane) hydrochloride in 50 ml of water. 105 ml of water, 20 ml of feed 1 and 2 ml of feed 2 were initially taken in a 1 glass apparatus equipped with a stirrer and feed vessels, and polymerization was carried out at 65° C. for 10 minutes with stirring. Thereafter, feed 1 was metered in over 4 hours and feed 2 over 6 hours at the same temperature and stirring was then continued for a further hour. A slightly cloudy solution of a polymer which had a K value of 54 and which became completely clear on dilution to 20% by weight was obtained.

EXAMPLE 12

A mixture of 112 g of a 70% strength solution of a monomer prepared similarly to Example 1 but using lactic acid instead of phosphoric acid, 115 g of N-vinylpyrrolidone, 0.39 g of 2-mercaptoethanol and 58 ml of water was brought to pH 7.5 with about 17 ml of 10% strength sodium hydroxide solution and served as feed 1. Feed 2 was a solution of 1.36 g of 2,2'-azobis-(amidinopropane) hydrochloride in 30 ml of water. 150 ml of water, 20 ml of feed 1 and 2 ml of feed 2 were initially taken in a 1 glass apparatus equipped with a stirrer and feed vessels, and polymerization was carried out at 65° C. for 10 minutes with stirring. At this temperature, feed 1 was then metered in over 4 hours and feed 2 over 6 hours and stirring was continued for a further hour. A solution of a polymer having a K value o 59 was obtained.

EXAMPLE 13

A mixture of 156 g of a 57% strength solution of a monomer prepared similarly to Example 1 but using citric acid instead of phosphoric acid, 90 g of N-vinylpyrrolidone, 0.36 g of 2-mercaptoethanol and 35 ml of water was brought to pH 7.5 with about 25 ml of 10% strength sodium hydroxide solution and served as feed 1. Feed 2 was a solution of 1.25 g of 2,2'-azobis-(2-amidinopropane) hydrochloride in 50 ml of water. 90 ml of water, 20 ml of feed 1 and 2 ml of feed 2 were initially taken in a 1 glass apparatus equipped with a stirrer and feed vessel and polymerization was carried out at 65° C. for 10 minutes with stirring. Thereafter, feed 1 was added in the course of 4 hours and feed 2 in the course of 6 hours and stirring was continued for a further hour. A slightly cloudy solution of a polymer which had a K value of 46 and became completely clear on dilution to 20% by weight was obtained.

EXAMPLE 14

350 g of a monomer solution according to Example 1 were brought to pH 8.0 with 150 ml of 10% strength sodium hydroxide solution and served as feed 1. Feed 2 was a solution of 1.35 g of tert.-butyl perpivalate in 50 g of isopropanol. 100 ml of water, 90 ml of feed 1 and 3 ml of feed 2 were initially taken in a 1 glass apparatus and polymerization was carried out at 70° C. for 10 minutes with stirring. Thereafter, feed 1 was added in the course of 4 hours and feed 2 in the course of 6 hours and stirring was continued for a further hour. Distilling off the isopropanol gave a slightly cloudy solution of a polymer having a K value of 22 . Use Example and comparison of the different corrosion properties:

4 mixtures were prepared according to the following recipe for cosmetic hair foams (parts by weight in each case):

| | |
|---|---|
| Cationic polymer (based on solids) | 1.2 |
| Fatty alcohol oxyethylate with 25 EO (Ceteareth 25) | 0.2 |
| Nonylphenol oxyethylate with 14 EO (Nonoxynol 14) | 0.1 |

| -continued | |
|---|---|
| Fatty acid diethanolamide (Cocamide-DEA) | 0.1 |
| Perfume/Nonoxynol 14 (1:2) | 0.3 |
| Distilled water | 78.1 |
| Absolute ethanol | 10.0 |
| Propane/butane (40:60) | 10.0 |

The cationic polymers used were
(a) a commercial copolymer of vinylpyrrolidone and 3-methyl-1-vinylimidazolium chloride (70 : 30)
(b) as for (a) but with a ratio of 50 : 50,
(c) novel copolymer of Example 6 and
(d) a commercial copolymer of vinylpyrrolidone and β-(trimethylammonium) ethyl methacrylate methosulfate (85 : 15).

The mixture was filled into tinplate cans, such as those usually employed in the cosmetics industry for noncorrosive formulations, and was stored at 40° C. The can was tested for corrosion after 4, 8 and 12 weeks.

The results are summarized in the table below:

TABLE

| | (a) | (b) | (c) | (d) |
|---|---|---|---|---|
| 4 weeks | corrosion at the base seam and in the gas space | corrosion at the base seam and in the gas space | no corrosion | corrosion at the base seam and in the gas space |
| 8 weeks | corrosion at the joint in the gas space and at the valve disk | rusted through | slight corrosion in the gas space | corrosion at the base seam, in the gas space and at the valve disk |
| 12 weeks | pronounced corrosion at the joint, in the gas space and at the valve disk | rusted through | slight corrosion in the gas space | corrosion at the base seam, in the gas space and at the valve disk |

In view of the corrosion behavior, the novel polymer is substantially superior for practical use.

We claim:
1. A water-soluble cationic homopolymer obtained from a water-soluble monomer having a polymerizable olefinic double bond and a quaternary nitrogen atom, of the formula I

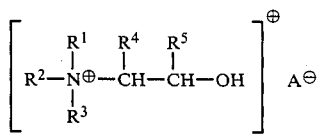

where $R^1$ is alkenyl of 2 to 4 carbon atoms or a radical of the formula II

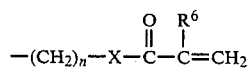

where n is an integer from 1 to 18, X an NH group and $R^6$ is hydrogen or methyl, $R^2$ is alkyl of 1 to 18 carbon atoms or hydroxyalkyl of 2 to 18 carbon atoms, $R^3$ is alkenyl of 2 to 4 carbon atoms or alkyl of 1 to 18 carbon atoms or hydroxyalkyl of 2 to 18 carbon atoms, or the radicals $R^1$, $R^2$ and $R^3$ together with the quaternary nitrogen atom form a 5-membered or 6-membered heterocyclic ring which is substituted by a polymerizable olefinic double bond and may contain a further nitrogen atom and may contain one or two alkyl radicals of 1 to 4 carbon atoms as substituents, and $R^4$ and $R^5$ are each hydrogen or alkyl of 1 to 28 carbon atoms or are each methyl which is substituted by alkoxy where alkyl is of 1 to 10 carbon atoms, and $A\ominus$ is one equivalent of an anion, except for halide, by free radical polymerization.

2. A water-soluble homopolymer obtained from a monomer of the formula I as claimed in claim 1, where $R^1$ is allyl or methallyl or a radical of the formula II having the meanings stated in claim 1, and n is from 2 to 6, $R^2$ is alkyl of 1 to 4 carbon atoms or hydroxyalkyl of 2 to 4 carbon atoms, $R^3$ is allyl or methallyl or alkyl of 1 to 4 carbon atoms or hydroxyalkyl of 2 to 4 carbon atoms, or $R^1$, $R^2$ and $R^3$ together with the quaternary nitrogen atom form 2- or 4-vinylpyridine or N-vinylimidazole which may be substituted by methyl, and $R^4$ and $R^5$ are each hydrogen, alkyl of 1 to 16 carbon atoms or methyl which is substituted by alkoxy where alkyl is of 1 to 10 carbon atoms, and not more than one of the radicals $R^4$ and $R^5$ may be replaced by an organic radical, and $A\ominus$ is one equivalent of an anion except for halide, free radical polymerization.

3. A water-soluble copolymer obtained from 2-98% by weight of a monomer of the formula I as defined in claim 1 or 2 and 98-2% by weight of a polymerizable water-soluble unsaturated comonomer, the percentages being based on the total weight of the monomers, by free radical polymerization.

4. A water-soluble copolymer as claimed in claim 3, wherein a hydroxyalkyl acrylate or hydroxyalkyl methacrylate where hydroxyalkyl is of 2 to 4 carbon atoms or an N-vinylamide selected from the group consisting of N-vinylpyrrolidone, N-vinylcaprolactam, N-vinylformamide, N-vinylacetamide and N-methyl-N-vinylacetamide is copolymerized as the water-soluble comonomer.

5. A water-soluble copolymer as claimed in claim 3, obtained from 2-98% by weight of a monomer of the formula I and 98-2% by weight of a polymerizable water-soluble unsaturated comonomer selected from the group consisting of acrylamide, methacrylamide, N-methylolacrylamide and N-methylolmethacrylamide.

* * * * *

UNITED STATES PATENT AND TRADEMARK OFFICE
CERTIFICATE OF CORRECTION

PATENT NO. : 4,859,756

DATED : August 22, 1989

INVENTOR(S) : Hans-Helmut Goertz, et al.

It is certified that error appears in the above-identified patent and that said Letters Patent is hereby corrected as shown below:

Title page:

The second Foreign Application Priority Data is incorrect
"Jul. 31, 1987  [DE]  Fed. Rep. Germany  ...........3725428"
should be:

--Jul. 31, 1987  [DE]  Fed. Rep. Germany  ........3725427--

Signed and Sealed this

Nineteenth Day of June, 1990

Attest:

HARRY F. MANBECK, JR.

*Attesting Officer*   *Commissioner of Patents and Trademarks*